United States Patent [19]

Mueller et al.

[11] Patent Number: 4,959,364

[45] Date of Patent: Sep. 25, 1990

[54] METHOD OF TREATING INFLAMMATION, ALLERGY, ASTHMA AND PROLIFERATIVE SKIN DISEASE USING HETEROCYCLIC AMIDES

[75] Inventors: Richard A. Mueller, Glencoe; Richard A. Partis, Evanston, both of Ill.

[73] Assignee: G. D. Searle & Co., Chicago, Ill.

[21] Appl. No.: 435,230

[22] Filed: Nov. 13, 1989

Related U.S. Application Data

[60] Division of Ser. No. 224,647, Jul. 27, 1988, abandoned, which is a continuation of Ser. No. 809,964, Dec. 20, 1985, abandoned, which is a continuation-in-part of Ser. No. 698,047, Feb. 4, 1985, abandoned.

[51] Int. Cl.$^5$ .................. A61K 31/40; A61K 31/445; A61K 31/505; A61K 31/535
[52] U.S. Cl. .................. 514/237.5; 514/255; 514/423; 514/211; 514/212; 514/218; 514/183; 514/330
[58] Field of Search .................. 514/255, 237.5, 423, 514/211, 218, 212, 183, 330

[56] References Cited

U.S. PATENT DOCUMENTS

| | | | |
|---|---|---|---|
| 3,907,792 | 9/1975 | Mieville | 540/575 |
| 4,029,812 | 6/1977 | Wagner | 514/575 |
| 4,076,841 | 2/1978 | Wagner | 564/162 |
| 4,134,996 | 1/1979 | Dunbar | 514/654 |
| 4,528,286 | 7/1985 | Moller | 546/226 |

Primary Examiner—Mary C. Lee
Assistant Examiner—Jacqueline Haley
Attorney, Agent, or Firm—Mary Jo Kanady; Paul D. Matukaitis

[57] ABSTRACT

The compounds of this invention are heterocyclic amides represented by the formula:

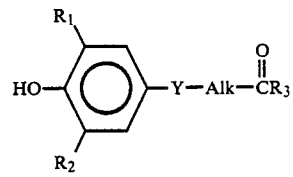

wherein: $R_1$ $R_2$ are the same or different members of the group consisting of halo, phenyl, substituted phenyl and a

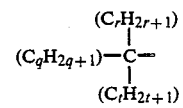

group wherein q, r and t are independently an integer of from 1 to 8 provided that $q+r+t$ is equal to or less than 10; y is thio, sulfinyl or sulfonyl; Alk is straight or branched chain lower alkylene, and $R_3$ is a heterocyclic amine represented by the formula:

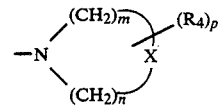

wherein $R_4$ is selected from the group consisting of hydrogen, lower alkyl, phenyl, substituted phenyl, benzyl, substituted benzyl, carboxyl or carboxyloweralkyl; X is selected from the group consisting of N—$R_4$, O and $CH_2$; m is 2 or 3; n is 2 or 3 when X is O or N—$R^4$, and n is 1 to 3 when x is $CH_2$; p is 0 to 2; and the pharmaceutically acceptable salts thereof. The compounds are anti-inflammatory and anti-allergy agents.

12 Claims, No Drawings

METHOD OF TREATING INFLAMMATION, ALLERGY, ASTHMA AND PROLIFERATIVE SKIN DISEASE USING HETEROCYCLIC AMIDES

This is a division of application Ser. No. 224,647, filed July 27, 1988, now abandoned which is a continuation of application Ser. No. 809,964 filed on Dec. 20, 1985 now abandoned which is a continuation-in-part of application Ser. No. 698,047 filed Feb. 4, 1985, now abandoned.

BACKGROUND OF THE INVENTION

A. Field of the Invention

The present invention relates to novel heterocyclic amides and more particularly relates to heterocyclic amides which are 5-lipoxygenase inhibitors and are useful as anti-inflammatory and anti-allergy agents.

It is well recognized that arachidonic acid and its analogs, unsaturated fatty acids, are the precursors of prostaglandins, thromboxanes, the 5-, 11-, 12- and 15-hydroxyeicosatetraenoic acids (HETEs, DIHETEs, TRIHETES) and hydroperoxyeicosatetraenoic acids (HPETEs) and the leukotrienes, all of which have profound physiological effects. The leukotrienes, which are produced via the 5-lipoxygenase pathway, are the major contributors to the onset of the symptoms of asthma, and mediators for immediate hypersensitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A) SRS-A consists of leukotrienes (LT) known as $A_4$, $B_4$, $C_4$, $D_4$, $D_5$ and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. The infiltration of eosinophils is one of the histologic features of a variety of allergic reactions.

With the exception of benoxaprofen, which has 5-lipoxygenase inhibition activity, aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced pro-inflammatory effects. Administration of the NSAIDs alone can produce allergic reactions including bronchospastic reactivity; skin rashes; syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the arachidonic acid cascade and the significance and interaction of the 5-lipoxygenase and other arachidonic acid cascade conversion products in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides heterocyclic amides which are metabolically stable inhibitors of the 5-lipoxygenase pathway and are useful in the treatment of asthma and other allergy and hypersensitivity reactions, and many types of inflammation.

To date, benoxaprofen has been the only commercial anti-inflammatory agent which has 5-lipoxygenase inhibition activity. Prior to its withdrawal from the market because of untoward side effects, benoxaprofen was considered to represent a significant advance in the treatment of crippling arthritis and psoriasis. Thus, there remains a longstanding need for agents which block the mechanisms responsible for inflammation and allergic reactions, and which can be safely employed to treat, for example, arthritis, asthma, psoriasis and other dermatoses, allergic reactions and other 5-lipoxygenase mediated conditions. A need also exists for agents which can be administered with the inhibitors of other lipoxygenase enzymes, e.g. cyclooxygenase, to mitigate their side effects and support their desirable medicinal properties.

See Bengt Samuelson, "Leukotrienes: Mediators of Immediate Hypersensitivity Reactions and Inflammation", *Science*, Vol. 220, pp. 568-575 (May 1983); Michael K. Bach, "Inhibitors of Leukotriene Synthesis and Action", *The Leukotrienes, Chemistry and Biology*, pp 163-194 (Academic Press, Inc., 1984); C. W. Lee et al., "Human Biology and Immunoreactivity of Leukotrienes", *Advances in Inflammation Research*, Volume 6, pp 219-225 (Raven Press, N.Y., 1984); Editorial, "Leukotrienes and other Lipoxygenase Products in the Pathegonesis and Therapy of Psoriasis and Dermatoses", *Arch. Dermatol.*, Vol. 119, pp 541-547 (July, 1983); Robert A. Lewis et al., "A Review of Recent Contributions on Biologically Active Products of Arachidonate Conversion", *Int. J. Immunopharmac.*, Vol. 4, No. 2, pp 85-90 (1982); Michael K. Bach, *Biochemical Pharmacology*, Vol. 23, No. 4, pp 515-521 (1984); E. L. Becker, *Chemotactic Factors of Inflammation*, pp 223-225 (Eliver Science Publishers B.V., Amsterdam, 1983); P. Sharon and W. F. Stenson, *Gastroenterology*, Vol. 84, 454 (1984); and M. W. Musch, et al., *Science*, Vol. 217, 1255 (1982).

The present invention provides compounds which block the 5-lipoxygenase pathway of the arachidonic acid cascade, block the formation of the leukotrienes therefore responsible for the allergy and inflammation, and hence and represent a new class of therapeutic agents which are useful in the treatment of allergic and hypersensitivity reactions and inflammation, alone, or in combination with other oxygenase inhibitors such as the non-steroidal anti-inflammatory agents (cyclooxygenase inhibitors).

B. Prior Art

Wagner et al. U.S. Pat. No. 4,029,812, and related U.S. Pat. Nos. 4,076,841 and 4,078,084 which issued from divisional applications of the -812 application, all assigned to The Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels.

The Wagner et al. and related compounds have also been reported in the literature as plasticizers and pesticides. See for Example, *Khim. Tekhnol.* 20(4), 568–574 (1977); German Offenlegenschrift No. DE 2716125(1977); *Pestic. Biochem. Physiol.* 1979, 12(1), 23–30. *Chem. Abs.* 90(19):151802x is of interest.

SUMMARY

The compounds of this invention are heterocyclic amides represented by the formula

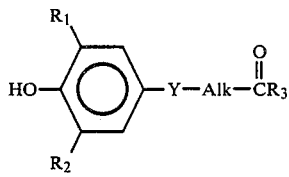

wherein: $R_1$ and $R_2$ are the same or different members of the group consisting of halo, phenyl, substituted phenyl and a

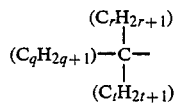

group wherein q, r and t are independently an integer of from 1 to 8 provided that $q+r+t$ is equal to or less than 10; Y is thio, sulfinyl or sulfonyl; Alk is straight or branched chain lower alkylene, and $R_3$ is a heterocyclic amine represented by the formula:

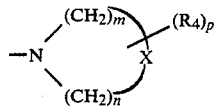

wherein $R_4$ is selected from the group consisting of hydrogen, lower alkyl, phenyl, substituted phenyl, benzyl, substituted benzyl, carboxyl or carboxyloweralkyl; X is selected from the group consisting of N—$R_4$, O and $CH_2$; m is 2 or 3; n is 2 or 3 when X is O or N—$R_4$ and n is 1 to 3 when X is $CH_2$; p is 0 to 2; and the pharmaceutically acceptable salts thereof.

Representative heterocyclic amines include, but are not limited to piperazine, morpholine, pyrrolidine, piperidine, pyrrolidinecarboxylic acid, methylpyrrolidine carboxylate, 2-methylpiperazine, 2,4-dimethylmorpholine, thiomorpholine and the like.

The compounds of the present invention are useful in the treatment of allergy and hypersensitivity reactions and inflammation. The compounds are particularly useful in the treatment of arthritis and other inflammatory joint disease, asthma, proliferative skin disease such as psoriasis, and the like, alone or in combination with one or more cyclooxygenase inhibitors.

DETAILED DESCRIPTION OF PREFERRED EMBODIMENTS

The compounds of the present invention are generally administered in oral or parenteral dosages of from 0.1 to 100 mg/kg, preferably 0.5 to 50 mg/kg daily, preferably in divided dosages, to patients suffering from allergic or hypersensitivity reactions or inflammation, and are preferably applied topically to patients suffering from proliferative skin disease such as psoriasis. The compounds may be administered as the sole therapeutic agent, or in combination with other agents such as cyclooxygenase inhibitors, particularly in patients who exhibit pro-inflammatory or allergic response to, for example, conventional non-steroidal anti-inflammatory agents. Parenteral, e.g., intravenous, administration is preferable if a rapid response is desired, as, for example, in some cases of asthma.

Generally speaking, synthesis of the compounds of this invention is accomplished by displacement of the halogen or tosylate on a halo or tosyl substituted aliphatic acyl heterocyclic amide by a thiol in the presence of a base. Addition of a thiol to the double bond of any alkenyl acyl heterocyclic amide is also an useful synthetic route. Alternatively, the displacement, via reaction with a thiol and base, can be carried out on a tosyl or halo substituted aliphatic carboxylic acid or ester which is then converted into the amide via reaction of the corresponding acid chloride with the desired heterocyclic amine. An ester is preferably hydrolyzed to the corresponding acid before conversion to the acid chloride by, for example, oxalyl chloride. The sulfones and sulfoxides are readily prepared by oxidation of a sulfide with for example, m-chlorobenzoic acid or sodium metaperiodate.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "halo", as used herein, includes chloro, bromo, iodo and fluoro.

The term "substituted phenyl" refers to phenyl having one or more substituents selected from the group consisting of amino, halo, hydroxy, lower alkyl, lower alkylaminoalkyl, lower dialkylaminoalkyl, trifluoromethyl, lower alkoxy, and the like for $R_4$ and halo, hydroxy, lower alkyl and lower alkoxy for $R_1$ and $R_2$.

The term "lower alkoxy" refers to alkoxy groups having from 1 to 6 straight or branched chain carbon atoms, i.e., methoxy, ethoxy, n-propoxy, tert-butoxy, etc.

The term "susbstituted benzyl" refers to benzyl groups having one or more substituents selected from the group consisting of halo, hydroxy, lower alkyl and lower alkoxy.

The term "pharmaceutically acceptable salt" refers to the physiologically acceptable acid addition salts of the amides of the present invention prepared by treating the compound with an appropriate acid as is well known in the art. Such salts include, but are not limited to, the hydrochloride, hydrobromide, sulfate, maleate, napsylate, oleate, succinate, palmitate, laureate, fumarate, phosphate, acetate, tartrate, stearate, nitrate, citrate, tosylate and like salts. The term also refers to the alkali metal, alkaline earth metal, ammonium and substituted ammonium salts of the carboxylic acid derivatives of this invention.

Preferred radicals represented by the group of the formula

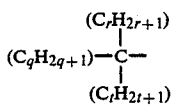

include tertiary alkyl moieties wherein q and r are preferably 1 or 2 and most preferred radical is represented by the group wherein q, r and t are 1, namely t-butyl. The groups represented by Y are preferably thio and sulfinyl, and most preferably thio.

The selective activity of the compounds of this invention was first determined using the following assays.

Test A—An in vitro inhibition of soybean 15-lipoxygenase assay is employed to check the specificity of selected 5-lipoxygenase inhibitors. The oxygen-uptake during the oxidation of arachidonic acid to 15-HPETE by soybean lipoxygenase is measured in the presence and absence of inhibitors, using nordihydroguaiaretic acid (NDGA) as a reference standard. Compounds which inhibit at 100 $\mu$M are tested further to determine the IC$_{50}$ values. "IC" stands for "inhibitory concentration".

Test B—Determination of anti-inflammatory, anti-allergy activity: in vitro inhibition of 5-lipoxygenase. The 100,000$\times$g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca$^{++}$ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are 1$\times$10$^{-4}$M. When the compound inhibits more than 50% of 5-HETE synthesis at 10$^{-4}$M, that compound is tested at multiple dose levels to determine the IC$_{50}$ value.

Test C—Inhibition of slow reacting substance (SRS) biosynthesis in cells. SRS synthesis by Rat Basophilic Leukemia Cell (RBL-1) cells is induced by incubation of cells with ionophore A23187 alone and in combination with the test compound. The SRS released into the culture media is measured by high pressure liquid chromatography, scintillation counting or bioassay. In the bioassay procedure the percent inhibition of SRS production is estimated by determining the doses of treated and control media needed in the tissue bath to produce equivalent contractions of segments of isolated guinea pig ileum. A compound that inhibits SRS biosynthesis by 50% or more is considered active at that concentration if an equivalent amount of the compound does not antagonize ileum contraction by SRS directly. If the compound directly inhibits the smooth muscle contractions, it will be considered inactive as an SRS biosynthesis inhibitor. Initial screening doses of test compounds are 1$\times$10$^{-4}$M and 1$\times$10$^{-5}$M.

Test D—In vitro inhibition of human platelet 12-lipoxygenase. A 40,000$\times$g supernatant of platelet lysate is incubated with [1-$^{14}$C]-labeled arachidonic acid in the presence and absence of test compound. The conversion product, 12-hydroxyeicosatetraenoic acid (12-HETE), is quantitated after isolation by thin-layer chromatography. Compounds, initially screened at 100 $\mu$M concentration, which inhibit the synthesis of 12-HETE by 30% or more, are considered active. IC$_{50}$ values are determined for active compounds.

Test E—In vitro inhibition of sheep seminal vesicle microsome cyclooxygenase. Arachidonic acid cyclooxygenase reaction rates, in the presence or absence of test compounds, are determined by monitoring oxygen uptake. Compounds which inhibit at 10$^{-4}$M are tested further to determine IC$_{50}$ values.

The following examples further illustrate the present invention.

EXAMPLE 1

Preparation of 3,5-bis(1,1-dimethylethyl)-4-hydroxyphenylthiocyanate

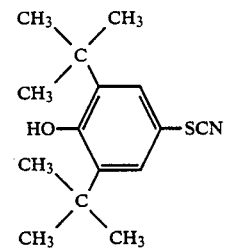

To a three-necked, round bottom 5 L flask, equipped with a mechanical stirrer, gas inlet, thermometer and gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into a 2 L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°–63° C.

Analysis calc. for C$_{15}$H$_{21}$NSO: Theory: C, 68.40; H, 8.03; N, 5.32; S, 12.17. Found: C, 68.85; H, 8.05; N, 5.29; S, 12.12.

EXAMPLE 2

Preparation of
2,6-bis(1,1-dimethylethyl)-4-mercaptophenol

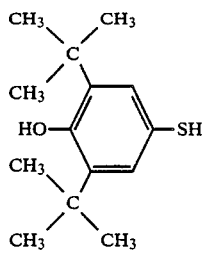

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to Yield a white powder which was recrystallized from methanol/water and dried to yield 43.3 g of the desired product. NMR confirmed the identity of the product.

EXAMPLE 3

1-methyl-4-(1-oxo-2-propenyl)piperazine

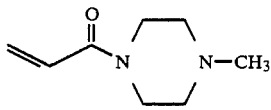

A solution of acryloyl chloride (9 g, 0.10 mole) in ethyl ether (20 ml) was added dropwise to a stirring, cold solution of N-methylpiperazine (10 g, 0.10 mole) and triethylamine (30.6 ml, 0.22 mole) in ethyl ether (150 ml) over a thirty minute period. An additional 75 ml of ethyl ether was added and the reaction stirred for 72 hours. The resulting white solid was filtered and washed well with ethyl ether. The ethyl ether was collected, combined with the filtrate and the solvent evaporated on a rotary evaporator to yield 9.5 g of product as an orange oil. NMR confirmed the structure of the product.

EXAMPLE 4

Preparation of
1-[3-[3,5-bis(1,1-dimethylethyl)-4-hydroxyphenyl]thio]-1-oxopropyl]-4-methylpiperazine

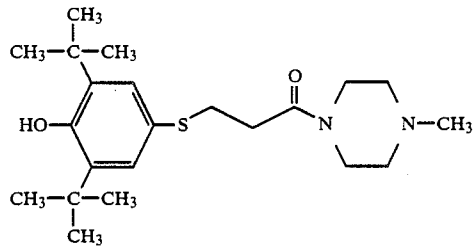

2,6-bis(1,1-Dimethylethyl)-4-mercaptophenol (2.15 g, 0.009 mole) and 1-methyl-4-(1-oxo-2-propenyl)piperazine (1.39 g, 0.009 mole) were dissolved in methanol (75 ml). Triethylamine (1.5 ml) was added and the reaction stirred at room temperature for twelve hours. The solvent and triethylamine were removed on a rotary evaporator to give an oil. The product was purified by chromatography on silica gel, eluting with hexane/ethyl acetate. The resulting product (0.68 g) was dried in a vacuum pistol for 72 hours under an ethyl acetate reflux.

Elemental Analysis for $C_{22}H_{36}N_2O_2S$ (392.6): Calc.: C, 67.30; H, 9.24; N, 7.14; S, 8.17. Found: C, 67.42; H, 9.24; N, 7.05; S, 8.30.

EXAMPLE 5

Preparation of
1-[3-[3,5-bis(1,1-dimethylethyl-4-hydroxyphenyl]thio]-1-oxopropyl]-4-methylpiperazine monohydrochloride

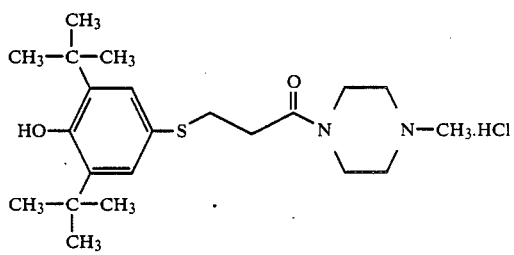

Following the procedure of Example 4, 2,6-bis-(1,1,-dimethylethyl)-4-thiophenol (1.19 g, 0.005 mole), 1-methyl-4-(1-oxo-2-propenyl)piperazine and triethylamine (0.5 ml) were combined and reacted for twelve hours. The solvents were removed under a nitrogen stream and the reaction chromatographed on silica. The product was collected, the solvents evaporated under a nitrogen stream and the resulting oil taken up in ethyl ether and a saturated hydrogen chloride-isopropanol solution added dropwise. After stirring for 12 hours, the hydrochloride salt as a white solid was filtered to yield 1.3 g of product. The product was dried in vacuo. m.p. about 201°–203° C. (429.05).

Elemental analysis for $C_{22}H_{37}N_2O_2SCl$ (429.06): Calc.: C, 61.59; H, 8.69; Cl, 8.26; N, 6.53; S, 7.47. Found: C, 61.83; H, 8.56; Cl, 8.50; N, 6.52; S, 7.49.

EXAMPLE 6

Preparation of 4-(1-oxo-2-propenyl)morpholine

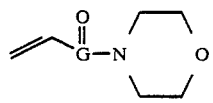

A solution of morpholine (8.7 g, 0.1 mole) and triethylamine (15.3 ml, 0.1 mole) in ethyl ether (100 ml) was cooled to +5° C. A solution of acryloyl chloride (9.0 g, 0.10 mole) in 25 ml of ethyl ether was added dropwise over a 30 minute period, resulting in the formation of a white solid. An additional 100 ml of ethyl ether was added and the reaction stirred for 72 hours at room temperature. The white solid was filtered and washed well with ethyl ether. The ethyl ether wash and filtrate were combined and solvent removed, leaving an orange oil which was transferred to a 50 ml Erlenmeyer flask and dried overnight under nitrogen to yield 11.5 g of product. The structure was confirmed by NMR.

EXAMPLE 7

Preparation of
4-[3-[3,5-bis(1,1-dimethylethyl)-4-hydroxyphenyl]thio-1-oxopropyl]morpholine

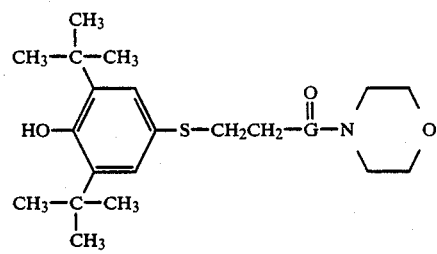

Following the procedure of Example 4, 2,6-bis-(1,1-dimethylethyl)4-mercaptophenol (2.389, 0.01 mole) and (1-oxo-2-propenyl)morpholine (1.41 g, 0.01 mole) in methanol (75 ml) were combined with triethylamine (1.5 ml) and stirred for 12 hours at room temperature. The solvent was evaporated under a nitrogen stream leaving an orange oil which was chromatographed over silica. The product was recrystallized from a mixture of hexane, ethyl ether and methanol and the resulting white solid dried to yield the title compound, m.p. about 136.5°–137.5° C.

Analysis calc. for $C_{21}H_{33}NO_3S$ (379.56): Calc.: C, 66.45; H, 8.76; N, 3.69; S, 8.45. Found: C, 66.88; H, 8.87; N, 3.53; S, 8.52.

EXAMPLE 8

1-(1-oxo-2-propenyl)-4-(phenylmethyl)piperazine

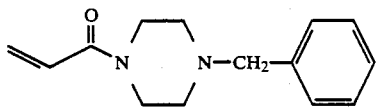

A solution of acryloyl chloride (4.52 g, 0.05 mole) in 25 ml of ethyl ether was added to a cold solution of 1-benzylpiperazine (8.8 g, 0.05 mole) and triethylamine (30 ml, 0.20 mole) in 500 ml of ethyl ether. A white precipitate formed. The reaction mixture was stirred overnight, filtered and the precipitate washed well with ethyl ether. The solvent and triethylamine were removed and the product chromatrographed on silica, eluting with ethyl acetate/hexane [30:70(v/v)] to yield 1.5 g of the title compound. The structure was confirmed by NMR.

EXAMPLE 9

Preparation of
1-[3-[[3,5-bis(1,1-dimethylethyl)-4-hydroxyphenyl]thio]-1-oxopropyl]-4-(phenylmethyl) piperazine

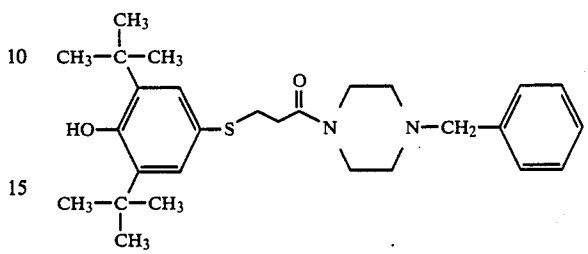

Following the method of Example 4, 2,6-bis-(1,1-dimethylethyl)-4-mercaptophenol (1.52 g, 0.0064 mole), 1-(1-oxo-2-propenyl)-4-phenylmethyl)piperazine (1.47 g, 0.0064 mole) and triethylamine (0.5 ml) were dissolved in 150 ml of methanol and stirred at room temperature for 12 hours. The solvent was removed on a rotary evaporator, and the reaction chromatographed on silica gel. The product was recrystallized from ethyl acetate and hexane. The resulting white solid was filtered and dried overnight in a vacuum pistol at room temperature, m.p. about 92.5°–95° C., (468.70).

Analysis calc. for $C_{28}H_{40}N_2SO_2$: Calc.: C, 71.75; H, 8.60; N, 5.98; S, 6.84. Found: C, 71.67; H, 8.69; N, 6.04; S, 6.87.

EXAMPLE 10

Preparation of
1-[3-[[3,5-bis(1,1-dimethylethyl)-4-hydroxyphenyl]thio]-1-oxopropyl]-4-(phenylmethyl)piperazine monohydrochloride

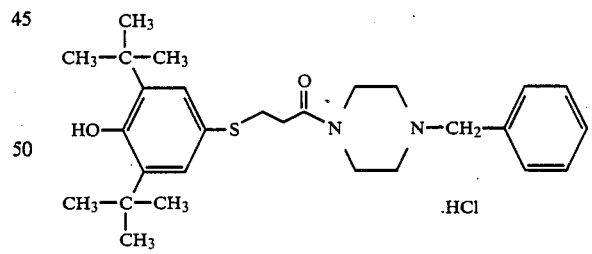

1-[3-[[3,5-bis(1,1-Dimethylethyl)-4-hydroxyphenyl]-thio]-1-oxopropyl]-4-(phenylmethyl)piperazine (2.0 g) was dissolved in 700 ml of ethyl ether. A saturated solution of hydrogen chloride in isopropanol was added dropwise with rapid stirring, and the reaction stirred for 12 hours. The hydrochloride salt formed as a white solid which was filtered, and air dried to yield 2.05 g of product, m.p. ca. 214°–216.5° C.

Analysis calc. for $C_{28}H_{41}N_2O_2ClS$ (505.16): Cald.: C, 66.57; H, 8.18; Cl, 7.02; N, 5.55; S, 6.35. Found: C, 66.54; H, 8.14; Cl, 7.39; N, 5.50; S, 6.50.

EXAMPLE 11

Preparation of methyl 1-(1-oxo-2-propenyl)-2-pyrrolidinecarboxylate

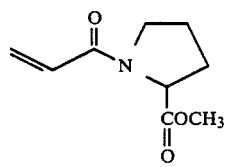

L-Proline methyl ester hydrochloride (8.27 g, 0.05 mole) was dissolved in 250 ml of methylene chloride and triethylamine (40 ml, 0.28 mole) added thereto. The solution was filtered to remove the precipitate and cooled to 5° C. Over a period of 30 minutes, a solution of acryloyl chloride (4.52 g, 0.05 mole) was added to the cooled solution, the reaction allowed to warm to room temperature and stirred for 12 hours. Ethyl ether (100 ml) was then added to the solution and the resulting white solid filtered. An additional 200 ml of ethyl ether was added and a small amount of tan solid filtered out. The solvents were evaporated, and the resulting oil chromatographed on silica to isolate the product. The product was dried in vacuo at room temperature for 72 hours. The structure was confirmed by NMR.

Analysis calc. for $C_9H_{13}NO_3$ (183.21): Calc.: C, 59.00; H, 7.15; N, 7.66. Found: C, 59.03; H, 7.25; N, 7.53.

EXAMPLE 12

Preparation of methyl-1-[3-[[3,5-bis(1,1-dimethylethyl)-4-hydroxyphenyl]thio]-1-oxopropyl]-2S-pyrrolidinecarboxylate

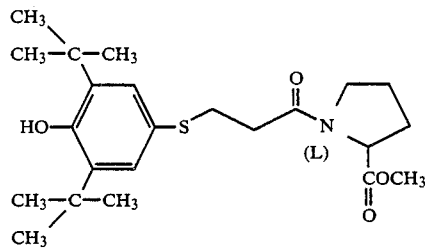

Following the procedure of Example 4, 2,6-bis-(1,1-dimethylethyl)-4-mercaptophenol (3.57 g, 0.015 mole), methyl 1-(1-oxo-2-propenyl)-2-pyrrolidinecarboxylate (2.7 g, 0.015 mole) and triethylamine (1 ml) were stirred at room temperature in methanol (100 ml). The solvent and triethylamine were evaporated under a nitrogen stream for 12 hours, and the residue chromatographed on silica, eluted with 10% ethyl acetate/hexane. The solvent was removed and the resulting product dried in a vacuum pistol under ethanol reflux for 12 hours to yield 3.8 g of the final product.

Analysis Calc. for $C_{23}H_{35}NSO_4$ (421.59): Calc.: C, 65.53; H, 8.37; N, 3.32; S, 7.60. Found: C, 65.54; H, 8.24; N, 3.29; S, 7.40.

EXAMPLE 13

Preparation of 1-[3-[[3,5-bis(1,1-dimethylethyl)4-hydroxyphenyl]thio]-1-oxopropyl]-2S-pyrrolidinecarboxylic acid

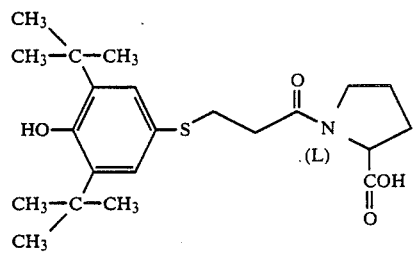

The title product of Example 12 (1.9 g) was dissolved in methanol (75 ml) and water added to the solution until it became cloudy. Lithium hydroxide monohydrate (1.5 g) was added and the mixture stirred at room temperature. The reaction was transferred to a round bottom flask and 50 ml of water added thereto. The solvent was removed on a rotary evaporator and the residue acidified with 10% hydrochloric acid. The product was extracted into ethyl ether (2×75 ml), washed with water (50 ml), dried over sodium sulfate, filtered and evaporated to an orange oil. The product was isolated by chromatography on silica, eluted with ethyl acetate/hexane to yield the product which was dried in vacuo.

Analysis calc. for $C_{22}H_{33}NO_4S$ (407.57): Calc.: C, 64.83; H, 8.16; S, 7.87; N, 3.46. Found: C, 64.67; H, 8.15; S, 7.50; N, 3.35.

EXAMPLE 14

Preparation of 1-(1-oxo-2-propenyl)pyrrolidine

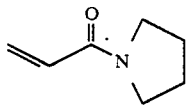

Acryloyl chloride (9 g, 0.1 mole) was added by syringe to ethyl ether (40 ml) and the solution cooled to −50° C. A solution of pyrrolidine (7.1 g, 0.1 mole) in ethyl ether (20 ml) was added dropwise. A solution of triethylamine (15.3 ml) was added slowly over 10 minutes. The reaction was slowly allowed to warm to room temperature and stirred for 12 hours. Water (50 ml) was added, the layers were separated and the aqueous layer extracted with ethyl ether (100 ml) and methylene chloride (2×75 ml), and combined with the organic layer above, dried over sodium sulfate, filtered, and the solvents removed to give an oil. The product was purified by chromatography on silica. The structure was confirmed by NMR.

EXAMPLE 15

Preparation of 1-[3-[[3,5-bis(1,1-diemthylethyl)-4hydroxyphenyl]thio]-1-oxopropyl]pyrrolidine

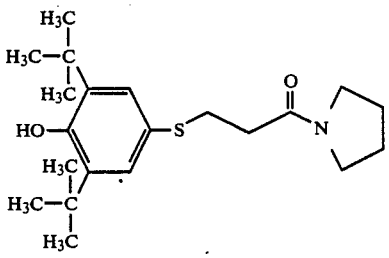

3,5-bis(1,1-Dimethylethyl)-4-hydroxyphenylthiocyanate (4.21 g, 0.016 mole) was dissolved in acetone (100 ml) and water (0.3 ml) added thereto. The solution was cooled in an ice bath and tri-n-butylphosphine (3.23 g, 0.016 mole) added via syringe over a 5 minute period. The ice bath was removed and the reaction brought to room temperature. Triethylamine (0.5 ml, 0.0036 mole) was added and the reaction stirred for 5 minutes. A solution of 1-(1-oxo-2-propenyl)pyrolidine (2.0 g, 0.016 mole) in acetone (20 ml) was added dropwise over a 10 minute period and the reaction stirred for 12 hours, then refluxed for an additional 5 hours. The solvent was evaporated and water (50 ml) added. The solution was extracted with ethyl ether (2×50 ml), and the ether extracts washed with water, dried over sodium sulfate and filtered. The solvent was removed in vacuo to give an oil. The product was isolated by chromatography on silica eluting with ethyl acetate/hexane. Recrystallization from ethyl acetate and hexane, filtering and drying the product for 12 hours in vacuo yielded the desired product, m.p. about 123.5°–124.5° C.

Analysis calc. for $C_{21}H_{33}NO_2S$ (363.56): Calc.: C, 69.38; H, 9.15; N, 3.85; S, 8.82. Found: C, 69.39; H, 9.01; N, 3.78; S, 8.68.

EXAMPLE 16

Preparation of 2'-hydroxy[1,1':3',1''-terphenyl]5'-yl thiocyanate

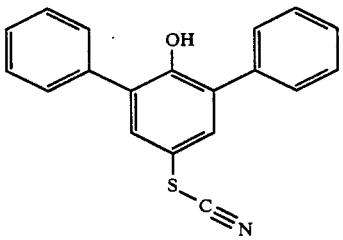

2,6,-Diphenylphenol (100.0 g, 0.406 mole) and ammonium thiocyanate (67.99 g, 0.893 mole) were suspended in methanol (150 ml) in a three-necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water (250 ml) and allowed to stand for 12 hours in the refrigerator. After filtering, the solid was dried in vacuo at 45° C. for 12 hours. The title compound was purified by chromatography on silica and recrystallized from hexane, m.p. about 104°–106.5° C.

Analysis calc. for $C_{19}H_{13}OSN$ (303.39): Calc.: C, 75.22; H, 4.32; N, 4.62; S, 10.57. Found: C, 75.12; H, 4.49; N, 4.65; S, 10.41.

EXAMPLE 17

Preparation of 5'-mercapto[1,1':3',1''-terphenyl]-2'-ol

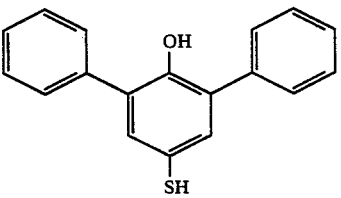

2'-Hydroxy[1,1':3',1''-terphenyl]-5'-yl thiocyanate (32.2 g, 0.106 mole) was dissolved in acetone (150 ml) and water (1.9 ml), stirred and cooled to −5° C. Triethylphosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica.

Analysis calc. for $C_{18}H_{14}OS$ (278.31): Calc.: C, 77.67; H, 5.07; S, 11.52. Found: C, 77.80; H, 5.19; S, 11.68.

EXAMPLE 18

Preparation of 1-[3-[(2'-hydroxy[1,1':3',1''-terphenyl]-5'-yl)thio]-1-oxopropyl]-4-(phenylmethyl)piperazine

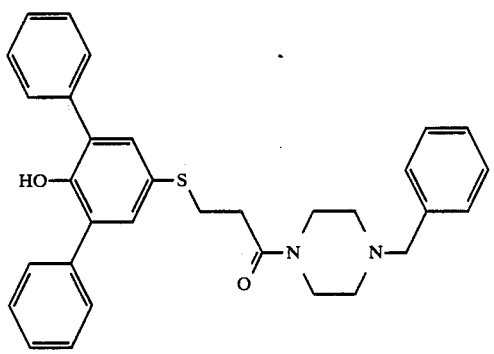

Following the procedure of Example 4, 1-(1-oxo-2-propenyl-4-phenylmethyl)piperazine (Example 8) (2.30 g, 0.01 mole) was dissolved in methanol (150 ml) and triethylamine (1 ml) added to the solution. The solution was flushed with argon several times, 5'-mercapto [1,1':3',1''-terphenyl]-2'-ol (2.77 g, 0.01 mole) added and the reaction stirred for 12 hours. The solvent was removed and the product isolated by chromatography to yield 1.5 g of product after drying in vacuo.

Analysis calc. for $C_{32}H_{32}N_2O_2S + 0.25\ C_4H_8O_2$: Calc.: C, 74.70; H, 6.46; N, 5.28; S, 6.04. Found: C, 74.75; H, 6.21; N, 5.51; S, 6.22.

EXAMPLE 19

Preparation of 1-(2-methyl-1-oxo-2-propenyl)pyrrolidine

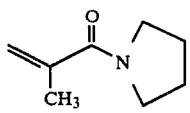

Under an argon atmosphere, pyrrolidine (3.55 g, 0.05 mole) was dissolved in ethyl ether (50 ml). Triethylamine (5.06 g, 0.05 mmole) was added and the solution cooled to and maintained at 0° C. 2-Methylacryloyl chloride (5.22 g, 0.05 mole), dissolved in ethyl ether (50 ml) was added to the reaction and the solution stirred overnight. Water (50 ml) was added, the layers were separated and the aqueous layer extracted with ethyl ether. The extracts were concentrated and the resulting product dried (6.77 g). The structure was confirmed by NMR.

EXAMPLE 20

Preparation of 1-[3-[[3,5-bis(1,1-dimethylethyl)-4-hydroxyphenyl]thio]-2-methyl-1-oxopropyl]pyrrolidine

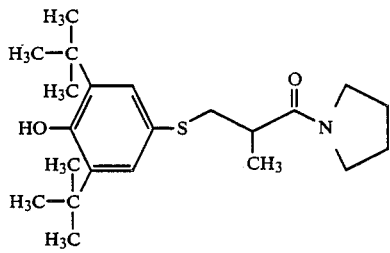

Following the procedure of Example 4, 2,6-bis(1,1-dimethylethyl)-4-mercaptophenol (2.0 g, 0.008 mole) and 1-(2-methyl-1-oxo-2-propenyl)pyrrolidine (1.11 g, 0.008 mole) were dissolved in toluene (20 ml) under an argon atmosphere and refluxed for 24 hours. The solvent was removed and the product purified by chromatography on silica, and recrystallized from hexane to yield the product as a white solid (0.65 g), m.p. 125°–126° C.

Analysis Calc. for $C_{25}H_{35}SNO_2$: Calc.: C, 69.98; H, 9.34; N, 3.71; S, 8.49. Found: C, 70.12; H, 9.05; N, 3.69; S, 8.73.

EXAMPLE 21

Preparation of 3,5-dichloro-4-hydroxyphenyl thiocyanate

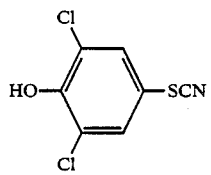

2,6-Dichlorophenol (100 g, 0.613 mole) and ammonium thiocyanate (102.73 g, 1.350 mole) were mixed in methanol and the solution cooled to 0° C. Chlorine gas was bubbled through the reaction, maintaining the temperature below 10° C. The solution turned a pale yellow color. The reaction was stirred for a total of 3 hours until acidic, at which time ammonia gas was bubbled through and the solution stirred for an additional three hours at 0° to 10° C. The reaction was poured into iced distilled water, and filtered, yielding approximately 20 g of a yellow solid which was dried overnight in vacuo. The filtrate was extracted with ethyl acetate, the extracts dried over magnesium sulfate and solvent removed in vacuo to yield approximately 100 g of crude product. Following purification by silica chromatography, the material was taken up in 1 liter of toluene, charcoal added, filtered and recrystallized from hexane to yield 55.03 g of product as a yellow solid, m.p. about 94.5°–97° C. The structure was confirmed by NMR.

EXAMPLE 22

Preparation of 2,6-dichloro-4-mercaptophenol

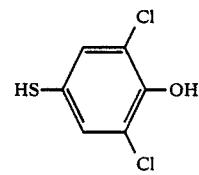

Following the method of Example 2, the title compound was prepared from 3,5-dicholoro-4-hydroxyphenyl thiocyanate. The structure was confirmed by NMR.

EXAMPLE 23

Preparation of 1-[3-[[3,5-dichloro-4-hydroxyphenyl]thio]1-oxopropyl]-4-(phenylmethyl)piperazine

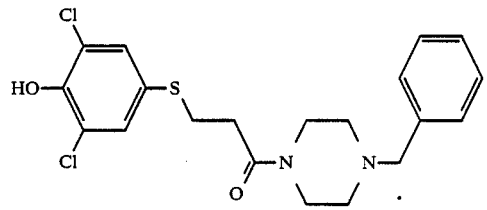

1-(1-Oxo-2-propenyl)-4-(phenylmethyl)piperazine (2.53 g, 0.011 mole) and 2,6-dichloro-4-mercaprophenol (2.15 g, 0.011 mole) were dissolved in methanol (75 ml). Triethylamine (1 ml) was added and the reaction stirred for 12 hours. The solvent was removed, and the product purified by chromatography on silica, eluting with ethyl acetate/hexane.

Analysis calc. for $C_{20}H_{22}O_2N_2Cl_2S$: Calc.: C, 56.47; H, 5.21; N, 6.59; Cl, 16.67; S, 7.54. Found: C, 56.59; H, 5.35; N, 6.46; Cl, 16.71; S, 7.33.

EXAMPLES 24–32

By replacing 2,6-bis(1,1-dimethyléthyl)-4-mercapto phenol with 2,6-dichloro-4-mercaptophenol in the procedure of Examples 4, 5, 7, 9, 10, 12, 13, 15, and 20, the following compounds are obtained:

EXAMPLE 24

1-[3-[(3,5-dichloro-4-hydroxyphenyl)thio]-1-oxopropyl]-4-methylpiperazine.

EXAMPLE 25

1-[3-[(3,5-dichloro-4-hydroxyphenyl)thio]-1-oxo-propyl-4-methylpiperazine monohydrochloride.

EXAMPLE 26

4-[3-[(3,5-dichloro-4-hydroxyphenyl)thio]-1-oxo-propyl]morpholine.

EXAMPLE 27

1-[3-[(3,5-dichloro-4-hydroxyphenyl)thio]-1-oxo-propyl]-4-(phenylmethyl)piperazine.

EXAMPLE 28

1-[3-[(3,5-dichloro-4-hydroxyphenyl)thio]-1-oxo-propyl]-4-(phenylmethyl)piperazine monohydrochloride.

EXAMPLE 29

Methyl 1-[3-[(3,5-dichloro-4-hydroxyphenyl)thio]-1-oxopropryl]-2S-pyrrolidinecarboxylate.

EXAMPLE 30

1-[3-[(3,5-dichloro-4-hydroxyphenyl)thio]-1-oxo-propyl]2S-pyrrolidinecarboxylic acid.

EXAMPLE 31

1-[3-[(3,5-dichloro-4-hydroxyphenyl)thio]-1-oxo-propyl]pyrrolidine.

EXAMPLE 32

1-[3-[(3,5-dichloro-4-hydroxyphenyl)thio]-2-methyl-1-oxopropyl]pyrrolidine.

EXAMPLES 33-41

By replacing 2,6-bis(1,1-dimethylethyl)-4-mercapto phenol with 5'-mercapto[1,1':3',1''-terphenyl]-2'-ol in Examples 4, 5, 7, 9, 10, 12, 13, 15 and 20, the following compounds are obtained.

EXAMPLE 33

1-[3-[(2'-hydroxy[1,1':3',1''-terphenyl]-5'-yl)thio]-1-oxopropyl]-4-methylpiperazine.

EXAMPLE 34

1-[3-[(2'-hydroxy[1,1':3',1''-terphenyl]-5'-yl)thio]-1-oxopropyl]-4-methylpiperazine monohydrochloride.

EXAMPLE 35

1-[3-[(2'-hydroxy[1,1':3',1''-terphenyl]-5'-yl)thio]-1-oxopropyl]-4-(phenylmethyl)piperazine.

EXAMPLE 36

1-[3-[(2'-hydroxy[1,1':3',1''-terphenyl]-5'-yl)thio]-1-oxopropyl]-4-(phenylmethyl)piperazine monohydrochloride.

EXAMPLE 37

1-[3-[(2'-hydroxy[1,1':3',1''-terphenyl]-5'-yl)thio]-1-oxopropyl]pyrrolidine.

EXAMPLE 38

1-[3-[(2'-hydroxy[1,1':3',1''-terphenyl]-5'-yl)-thio]-2-methyl-1-oxopropyl]pyrrolidine.

EXAMPLE 39

Methyl 1-[3-[(2'-hydroxy[1,1':3',1''-terphenyl]-5'-yl)thio]-1-oxopropyl]-2S-pyrrolidinecarboxylate.

EXAMPLE 40

1-[3-[(2'-hydroxy[1,1':3',1''-terphenyl]-5'-yl)-thio]-1-oxopropyl]-2S-pyrrolidinecarboxylic acid.

EXAMPLE 41

4-[3-[(2'-hydroxy[1,1':3',1''-terphenyl]-5'-yl)-thio]-1-oxopropyl]morpholine.

EXAMPLE 42

Preparation of 4-[[3,5-bis(1,1-dimethylethyl)-4-hydroxy phenyl]thio]butanoic acid

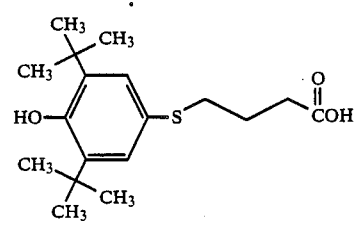

Potassium hydroxide flakes (2.52 g, 0.045 mole) were added to a clear solution of 2,6-bis(1,1-dimethylethyl)-4-mercaptophenol (3.57 g, 0.015 mole) and ethyl-4-bromobutyrate (3.23 g, 0.0165 mole) in acetone (10 ml). Water (20 ml) was added and the solution stirred for 1.5 hours, the solvent removed on a rotary evaporator and water (50 ml) added and extracted with ethyl ether (3×75 ml). The aqueous layer was acidified with concentrated hydrochloric acid, extracted with ethyl ether (2×50 ml), washed with water (50 ml), dried over sodium sulfate, filtered and the solvents removed, leaving an oil, which was purified by chromatography on silica, recrystallized from ethyl ether/Skellysolve B, filtered and the product dried in vacuo at room temperature for 12 hours, m.p. ca. 112°-113.5° C.

Analysis calc. for $C_{18}H_{28}O_3S$ (324.48): Calc.: C, 66.63; H, 8.70; S, 9.88. Found: C, 66.71; H, 8.74; S, 9.57.

EXAMPLE 43

Preparation of
1-[4-[[3,5-bis(1,1-dimethylethyl)-4-hydroxy phenyl]thio]-1-oxobutyl]-4-(phenylmethyl)piperazine.

4-[[3,5-bis(1,1-Dimethylethyl)-4-hydroxyphenyl]thio]butanoic acid is dissolved in benzene and the solution cooled to about 5° C. in an ice bath. A solution of oxalyl chloride in benzene is added dropwise over a period of about 5 minutes. The ice bath is removed and the solution is allowed to warm to room temperature and is stirred for about 5 hours. The benzene is evaporated and fresh benzene is added. Triethylamine and N-benzylpiperazine are added and the solution is stirred overnight. The benezene is evaporated on a rotary evaporator and the product is purified by chromatography on silica.

EXAMPLE 44

Preparation of 2-[[3,5-bis(1,1-dimethylethyl)-4-hydroxy phenyl]thio]pentanoic acid

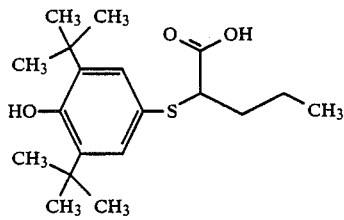

The title compound was prepared according to the method of Example 41 from potassium hydroxide flakes (3.36 g, 0.06 mole), 2,6-bis(1,1-dimethylethyl)-4-mercaptophenol (4.76 g, 0.02 mole) and ethyl-2-bromovalerate (4.18 g, 0.02 mole) in acetone (100 ml). The structure was confirmed by NMR.

EXAMPLE 45

Preparation of 1-[2-[[3,5-bis(1,1-dimethylethyl)-4-hydroxy phenyl]thio]-1-oxopentyl]-4-(phenylmethyl)piperazine.

The title compound of Example 44 is converted to its acid chloride and is reacted with N-benzylpiperazine by the method of Example 42 to give the title compound.

EXAMPLE 46

Preparation of 2-chloro-N-(N-benzylpiperazine)acetamide

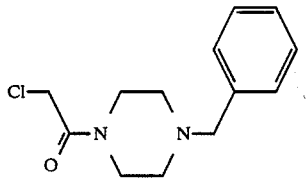

Chloroacetyl chloride in methylene chloride is cooled via an ice bath of 0° C. A solution of N-benzylpiperazine and triethylamine in methylene chloride is added dropwise over a period of 1 hour and the resulting solution stirred, and allowed to come to room temperature during a 20 hour period. 10% Hydrochloric acid is added and the layers are separated. The organic layer is washed with 1N hydrochloric acid and water, is dried over sodium sulfate, filtered and the solvent is removed to give the title compound.

EXAMPLE 47

Preparation of 1-[2-[[3,5-bis(1,1-dimethylethyl)-4-hydroxy-phenyl]thio]-1-oxoethyl]-4-(phenylmethyl)lpiperazine

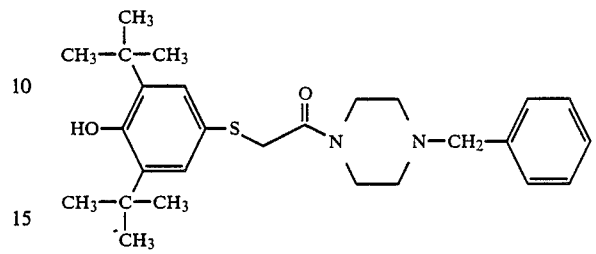

The title compound is prepared by dissolving the product of Example 46 and 2,6-bis(1,1-dimethylethyl)-4- mercaptophenol in acetonitrile under argon. Triethylamine is added to the solution with stirring at room temperature under argon for about 12 hours. The solution is acidified with 10% hydrochloric acid with stirring. It is extracted with ethyl acetate, the extracts combined, washed with water and dried over sodium sulfate. The solvent is removed on a rotary evaporator and the product is purified by chromatography on silica.

EXAMPLE 48

Preparation of 1-(1-oxo-2-butenyl)pyrrolidine

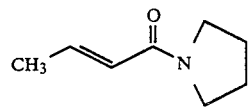

3-Methylacryloyl chloride was reacted with pyrrolidine by the method of Example 14 to give the title amide.

EXAMPLE 49

Preparation of 1-[3-[[3,5-bis(1,1-dimethylethyl)-4-hydroxyphenyl]thio]-1-oxobutyl]pyrrolidine

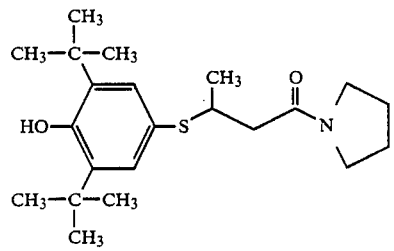

Following the procedure of Example 4, 2,6-bis(1,1-dimethylethyl)-4-mercaptophenol (2.0g, 0.008 mole) and 1-(1-oxo-2-butenyl)pyrrolidine (1.11g, 0.008 mole) were dissolved in methanol (20ml) under an argon atmosphere and refluxed for 24 hours. The solvent was removed and the product isolated by chromatography on silica, and recrystallized from hexane to yield the product as a white solid, m.p. about 95°–99° C.

Analysis calc. for $C_{25}H_{35}SNO_2$ Calc.: C, 69.98; H, 9.34; N, 3.71; S, 8.49. Found: C, 69.75; H, 9.33; N, 3.71; S, 8.55.

The active agents of this invention can be administered to animals, including humans, as pure compounds. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predetermined, therapeutically effective amount of one or more active agents and a pharmaceutically acceptable carrier or diluent. Generally speaking, solid oral unit dosage forms of a compound of this invention will contain from 1.75 to 750mg per tablet of drug.

The compounds of this invention exhibit both oral and parenteral activity and accordingly can be formulated in dosage forms for either oral or parenteral administration.

Solid oral dosage forms include capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds of this invention may also be formulated for topical or transdermal application using carriers which are well known in the art, as well as in aerosols or sprays for nasal administration.

The amount of active ingredient administered may be varied; however, it is necessary that the amount of active ingredient be such that a suitable dosage is given. The selected dosage depends upon the desired therapeutic effect, the route of administration and the duration of treatment. Generally speaking, oral dosages of from 0.1 to 100 mg/kg, and preferably from 0.5 to 50 mg/kg of body weight daily are administered to patients in need of such treatment, preferably in divided dosages, e.g. three to four times daily. In the case of acute allergic or hypersensitivity reactions, it is generally preferable to administer the initial dosage via the parenteral route, e.g. intravenous, and continue parenteral administration until the patient is stabilized, and can be maintained, if necessary on oral dosing.

In the case of psoriasis and other skin conditions, it is preferred to apply a topical preparation of a compound of this invention to the affected areas three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

When the compounds of this invention are co-administered with one or more cyclooxygenase inhibitors, they may conveniently be administered in a unit dosage form or may be administered separately. When the patient is allergic or hypersensitive to the cycloxygenase inhibitor, it is preferred to initiate therapy with a compound of this invention prior to administration of the cyclooxygenase inhibitor.

A typical tablet of this invention can have the following composition:

| Ingredient | Mg/tablet |
|---|---|
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

The invention claimed is:

1. A method of treating inflammation comprising administering to an animal in need of such treatment a therapeutically effective amount of a compound of the formula:

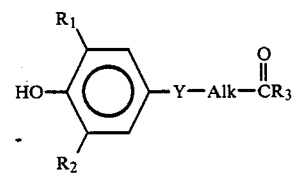

wherein: $R_1$ and $R_2$ are the same or different members of the group consisting of halo, phenyl, substituted phenyl and a

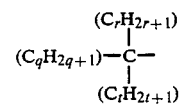

group wherein q, r and t are independently an integer of from 1 to 8 provided that $q + r + t$ is equal to or less than 10; Y is thio or sulfinyl; Alk is straight or branched chain lower alkylene; and $R_3$ is a heterocyclic amine represented by the formula:

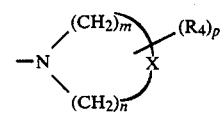

wherein $R_4$ is selected from the group consisting of hydrogen, lower alkyl, phenyl, substituted phenyl, benzyl, substituted benzyl, carboxyl or caboxyloweralkyl; X is selected from the group consisting of $N-R_4$, 0 and $-CH_2$; m is 2 or 3; n is 2 or 3 when X is 0 or $N-R_4$, and is 1 to 3 when X is $CH_2$; p is 0 to 2; or the pharmaceutical acceptable salts thereof.

2. A method according to claim 1 wherein $R_1$ and $R_2$ each are 1,1-dimethylethyl and Y is thio.

3. A method according to claim 2 wherein said compound is selected from the group consisting of 1-[3-[[3,5-bis(1,1-dimethylethyl)-4-hydroxyphenyl]thio]-1-oxopropyl]pyrrolidine;

methyl 1-[3-[[3,5-bis(1,1-dimethylethyl)-4-hydroxyohenyl)thio]-1-oxopropyl]-28-pyrrolidinecaboxylate;

1-[3-[[3,5-bis-(1,1-dimethylethyl)-4-hydroxyphenyl]-thio]-1-oxopropyl]-28-pyrrolidinecarboxylic acid or a pharmaceutically acceptable salt thereof;

1-[3-[[3,5-bis(1,1-dimethylethyl)-4-hydroxyphenyl]-thio]-1-oxopropyl]-4-methylpiperazine monohyrrochloride;

4-[3-[[3,5-bis(1,1-dimethylethyl)-4-hydroxyphenyl]-thio]-1-oxopropyl]morpholine;

1-[3-[[3,5-bis,(1,1-dimethylethyl)-4-hydroxyphenyl]-thio]-1-oxopropyl]-4-(phenylmethyl)piperazine or a pharmaceutically acceptable salt thereof;

1-[3-[[3,5-bis(1,1-dimethylethyl)-4-hydroxyphenyl]-thio]-1-oxopropyl]-4-(phenylmethyl)piperazine monohydrochloride;

1-[3-[[3,5-bis(1,1-dimethylethyl)-4-hydroxyphenyl]-thio]-2methyl-1-oxopropyl]pyrrolidine;

1-[3-[[3,5-bis(1,1-dimethylethyl)-4-hydroxyphenyl]-thio]-1-oxobutyl]pyrrolidine;

1-[3-[[3,5-dichloro-4-hydrocyphenyl]thio]-1-oxopropyl]-4-(phenylmethyl)piperazine or a pharmaceutically acceptable salt thereof; and 1-[3-[(2'-hydroxy[1,1'3'''1''-terphenyl]-5'-yl)thio]-1-oxopropyl]-4-(phenylmethyl) piperazine or a pharmaceutically acceptable salt thereof.

4. A method of treating allergic reactions comprising administering to an animal in need of such treatment a therapeutically effective amount of a compound of the formula

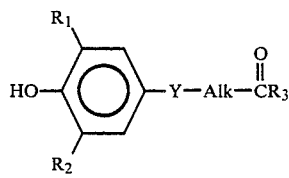

wherein: $R_1$ and $R_2$ are the same or different members of the group consisting of halo, phenyl, substituted phenyl and a

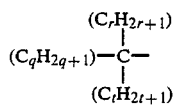

group wherein q, r and t are independently an integer of from 1 to 8 provided that q +r +t is equal to or less than 10; Y is thio or sulfinyl; Alk is straight or branched chain lower alkylene; and $R_3$ is a heterocyclic amine represented by the formula:

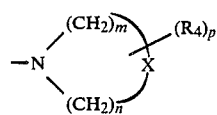

wherein $R_4$ is selected from the group consisting of hydrogen, lower alkyl, phenyl, substituted phenyl, benzyl, substituted benzyl, carboxyl or carboxyloweralkyl; X is selected from the group consisting of N—$R_4$, O and —$CH_2$; m is 2 or 3; n is 2 or 3 when X is O or N—$R_4$, and n is 1 to 3 when X is $CH_2$; p is 1 to 2; or the pharmaceutically acceptable salts thereof.

5. A method according to claim 4 wherein $R_1$ amd $R_2$ each are 1,1-dimethylethyl and Y is thio.

6. A method according to claim 5 wherein said compound is selected from the group consisting of 1-[3-[[3,5-bis(1,1-dimethylethyl)-4-hydroxyphenyl]thio]-1-oxopropyl]pyrrolidine;

methyl 1-[3-[[3,5-bis-(1,1-dimethylethyl)-4-hydroxyphenyl]thio]-1-oxopropyl]2S-pyrrolidinecarboxylate;

1-[3-[[3,5-bis-(1,1-dimethylethyl)-4-hydroxyphenyl]-thio]-1-oxopropyl]-2S-pyrrolidinecarboxylic acid or a pharmaceutically acceptable salt thereof;

1-[3-[[3,5-bis(1,1-dimethylethyl-4-hydroxyphenyl]thio]-1-oxopropyl]-4-methylpiperazine or a pharmaceutically acceptable salt thereof;

1-[3-[[3,5-bis(1,1-dimethylethyl)-4-hydroxyphenyl]-thio]-1-oxopropyl]-4-methylpiperazine monohydrochloride;

4-[3-[[3,5-bis(1,1-dimethylethyl)-4-hydroxyphenyl]-thio]-1-oxopropyl]morpholine;

1-[3-[[3,5-bis(1,1-dimethylethyl)-4-hydroxyphenyl]-thio]-1-oxopropyl]-4-(phenylmethyl)piperazine or a pharmaceutically acceptable salt thereof;

1-[3-[[3,5-bis(1,1-dimethylethyl)-4-hydroxyphenyl]-thio]-1-oxopropyl]-4-(phenylmethyl)piperazine monohydrochloride;

1-[3-[[3,5-bis(1,1-dimethylethyl)-4-hydroxyphenyl]-thio]-2-methyl-1-oxopropyl]pyrrolidine;

1-[3-[[3,5-bis(1,1-dimethylethyl)-4-hydroxyphenyl]-thio]-1-oxobutyl]pyrrolidine;

1-[3-[[3,5-dichloro-4-hydroxyphenyl]thio]-1-oxopropyl]-4-(phenylmethyl)piperazine or a pharmaceutical acceptable salt thereof; and 1-[3-[(2'-hydroxy[1,1':3',1''-terphenyl]-5,-yl)thio]-1-oxopropyl]-4-(phenylmethyl)piperazine or a pharmaceutically acceptable salt thereof.

7. A method of treating proliferate skin disease comprising administering to an animal in need of such treatment a therapeutically effective amount of a compound of the formula:

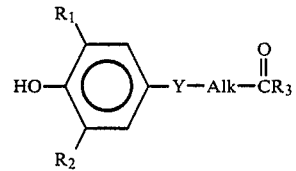

wherein $R_1$ and $R_2$ are the same or different members of the group consisting of halo, phenyl, substituted phenyl and a

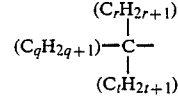

group wherein q, r and t are independently an integer of from 1 to 8 provided that q +r +t is equal to or less than 10; Y is thio or sulfinyl; Alk is straight or branched chain lower alkylene; and R3 is a heterocyclic amine represented by the formula:

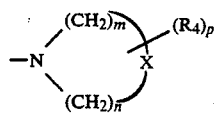

wherein R4 is selected from the group consisting of hydrogen, lower alkyl, phenyl, substituted phenyl, benzyl, substituted benzyl, carboxyl or carboxyloweralkyl; X is selected from the group consisting of N—R4, O and —CH2; m is 2 or 3; n is 2 or 3 when X is O or N-R4, and n is 1 to 3 when X is CH2; p is 0 to 2; or the pharmaceutically acceptable salts thereof.

8. A method according to claim 7 wherein $R_1$ and $R_2$ each are 1,1-dimethylethyl and Y is thio.

9. A method according to claim 8 wherein said compound is selected from the group consisting of 1-[3-[[3,5-bis(1,1-dimethylethyl)-4-hydroxyphenyl]thio]-1-oxopropyl]pyrrolidine;

methyl 1-[3-[[3,5-bis-(1,1-dimethylethyl)-4-hydroxyphenyl]thio]-1-oxopropyl]-2S-pyrrolidinecarboylate;

1-[3-[[3,5-bis-(1,1-dimethylethyl-4-hydroxyphenyl]-thio]-1-oxopropyl]-2S-pyrrolidinecarboxylic acid or a pharmaceutically acceptable salt thereof;

1-[3-[[3,5-bis,(1,1-dimethylethyl)-4-hydroxyphenyl]-thio]-1-oxopropyl]-4-(methylpiperazine or a pharmaceutically acceptable salt thereof;

1-[3-[[3,5-bis(1,1-dimethylethyl)-4-hydroxyphenyl]-thio]-1-oxopropyl]-4-methylpiperazine monohydrochloride;

4-[3-[[3,5-bis(1,1-dimethylethyl)-4-hydroxyphenyl]-thio]-1-oxopropyl]morpholine;

1-[3-[[3,5-bis(1,1-dimethylethyl)-4-hydroxyphenyl]thio-]-1-oxopropyl]-4-(phenylmethyl)piperazine or a pharmaceutically acceptable salt thereof;

1-[3-[[3,5-bis(1,1-dimethylethyl)-4-hydroxyphenyl]-thio]-1-oxopropyl]-4-(phenylmethyl)piperazine monohydrochloride;

1-[3-[[3,5-bis(1,1-dimethylethyl)-4-hydroxyphenyl]-thio]-2-methyl-1-oxopropyl]pyrrolidine;

1-[3-[[3,5-bis(1,1-dimethylethyl)-4-hydroxyphenyl]-thio]-1-oxobutyl]pyrrolidine;

1-]3-[[3,5-dichloro-4-hydroxyphenyl]thio]-1-oxopropyl]-4-(phenylmethyl)piperazine or a pharmaceutically acceptable salt, thereof; and, 1-[3-[(2'-hydroxy[1,1':3  "1"-terphenyl)-5'-yl)thio]-1-oxopropyl]-4-(phenylmethyl) piperazine or a pharmaceutically acceptable salt thereof.

10. A method of treating asthma comprising administering to an animal in need of such treatment a therapeutically effective amount of a compound of the formula:

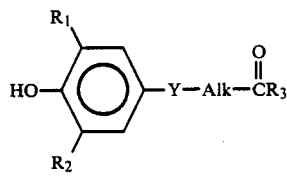

wherein: $R_1$ and $R_1$ are the same or different members of the group consisting of halo, phenyl, substituted phenyl and a

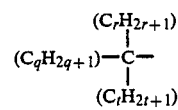

group when q, r and t are independently an integer of from 1 to 8 provided that q + r + t is equal to or less that 10; Y is thio or sulfinyl; Alk is a straight or branched chain lower alkylene; and R3 is a heterocyclic amine represented by the formula:

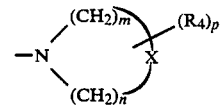

wherein R4 is selected from the group consisting of hydrogen, lower alkyl, phenyl, substituted phenyl, benzyl, substituted benzyl, carboxyl or carboxyloweralkyl; X is selected from the group consisting of N—R4, o and —CH2; m is 2 or 3; n is 2 or 3 when X is 0 or N—R4, and n is 1 to 3 when X is CH2; p is 0 to 2; or the pharmaceutically acceptable salts thereof.

11. A method according to claim 10 wherein $R_1$ and $R_2$ each are 1,1-dimethylethyl and Y is thio.

12. A method according to claim 11 wherein said compound is selected from the group consisting of 1-[3-[[3,5-bis(1,1-dimethylethyl)-4-hydroxyphenyl]thio]-1-oxopropyl]pyrrolidine;

methyl 1-[3-[[3,5-bis-(1,1-dimethylethyl)-4-hydroxyphenyl]thio]-1-oxopropyl]-2S-pyrrolidinecarboxylate;

1-[3-[[3,5-bis-(1,1-dimethylethyl)-4-hydroxyphenyl]-thio]-1-oxopropyl]-2S-pyrroliinecarboxylic acid or a pharmaceutically acceptable salt thereof;

1-[3-[[3,5-bis,(1,1-dimethylethyl)-4-hydroxyphenyl]-thio]-1-oxopropyl]-4-(methylpiperazine or a pharmaceutically acceptable salt thereof;

1-[3-[[3,5-bis(1,1-dimethylethyl)-4-hydroxyphenyl]-thio]-1-oxopropyl]-4-methylpiperazine monohydrochloride;

4-[3-[[3,5-1,1-dimethylethyl)-4-hydroxyphenyl]thio]-1-oxopropyl]morpholine;

1-[3-[[3,5-bis(1,1-dimethylethyl)-4-hydroxyphenyl]thio-]-1-oxopropyl]-4-(phenylmethyl)piperazine or a pharmaceutically acceptable salt thereof;

1-[3-[[3,5-bis(1,1-dimethylethyl)-4-hydroxyphenyl]-thio]-1-oxopropyl]-4-(phenylmethyl)piperazine monohydrochloride;

1-[3-[[3,5-bis(1,1-dimethylethyl)-4-hydroxyphenyl]-thio]-2-methyl-1-oxopropyl]pyrrolidine;

1-[3-[[3,5-bis(1,1-dimethylethyl)-4-hydroxyphenyl]-thio]-1-oxobutyl]pyrrolidine;

1-[3-[[3,5-dichloro-4-hydroxyphenyl]thio]-1-oxopropyl]-4-(phenylmethyl)piperazine or a pharmaceutically acceptable salt thereof; and , 1-[3-[(2'-hydroxy[1,1':3',1"-terphenyl]-5'-yl)thio]-1-oxopropyl]-4-(phenylmethyl) piperazine or a pharmaceutically acceptable salt thereof.

* * * * *

UNITED STATES PATENT AND TRADEMARK OFFICE
CERTIFICATE OF CORRECTION

PATENT NO. : 4,959,364

DATED : Sep. 25, 1990

INVENTOR(S) : Mueller et al.

Page 1 of 2

It is certified that error appears in the above-identified patent and that said Letters Patent is hereby corrected as shown below:

Column 1, line 38, reading "(SRS-A) SRS-A" should read
-- (SRS-A). SRS-A --
Column 8, the first structure, that portion of the structure reading Column 9, line 25, reading "(2.389" should read -- (2.38 g --.
Column 13, line 4, reading "-diemthylethyl)-4hydroxyphenyl]" should read -- -dimethylethyl-4-hydroxyphenyl] --.
Column 16, line 35, reading "thio]1-" should read -- thio]-1- --.
Column 19, line 56, reading "of" should read -- at --.
Column 20, line 5, reading "1piperazine" should read
-- piperazine --.
Column 23, lines 7-8, reading "-bis(1,1-dimethylethyl)-4-hydroxohenyl)thio]-1-oxopropyl]-28-" should read -- -bis-(1,1-dimethylethyl)-4-hydroxyphenyl]thio]-1-oxopropyl]-2S- --.
Column 23, line 11, reading "-28-" should read -- -2S- --.
Column 23, lines 14-15, reading "monohyrrochloride" should read -- monohydrochloride --.
Column 23, line 25, reading "-2methyl-" should read
-- -2-methyl- --.
Column 23, line 28, reading "-hydrocyphenyl]" should read
-- -hydroxyphenyl] --.
Column 23, line 31, reading "[1,1'3"1"-" should read
-- [1,1':3',1"- --.
Column 24, line 4, reading "p is 1 to 2" should read
-- p is 0 to 2 --.
Column 24, line 13, reading "-oxopropyl]2S-" should read
-- -oxopropyl]-2S- --.
Column 25, line 14, reading "CH2" should read -- $CH_2$ --.
Column 25, line 47, reading "1-]3-" should read -- 1-[3- --.

UNITED STATES PATENT AND TRADEMARK OFFICE
CERTIFICATE OF CORRECTION

PATENT NO. : 4,959,364
DATED : Sep. 25, 1990
INVENTOR(S) : Mueller et al.

It is certified that error appears in the above-identified patent and that said Letters Patent is hereby corrected as shown below:

Column 26, line 1, reading "$R_1$ and $R_1$" should read -- $R_1$ and $R_2$ --.

Column 26, line 10, reading "when" should read -- wherein --
Column 26, line 24, reading "o and" should read -- O and --.
Column 26, line 47, reading "5-1,1-" should read -- 5-bis(1,1- --.

Signed and Sealed this

Twenty-second Day of September, 1992

Attest:

DOUGLAS B. COMER

Attesting Officer     Acting Commissioner of Patents and Trademarks